US00PP09346P

United States Patent [19]

Shibata

[11] Patent Number: Plant 9,346

[45] Date of Patent: Oct. 31, 1995

[54] DAWN REDWOOD VARIETY "GOLDEN OJI"

[75] Inventor: Masaru Shibata, Kameyama, Japan

[73] Assignee: New Oji Paper Co., Ltd., Tokyo, Japan

[21] Appl. No.: 291,955

[22] Filed: Aug. 16, 1994

[51] Int. Cl.[6] ..... A01H 5/00

[52] U.S. Cl. ..... Plt./50.1

[58] Field of Search ..... Plt./50.1

*Primary Examiner*—James R. Feyrer

*Attorney, Agent, or Firm*—Armstrong, Westerman, Hattori, McLeland & Naughton

[57] ABSTRACT

A new variety, called 'Golden Oji', of 'Dawn Redwood' is valuable for landscape ornamental. The new variety has beautiful golden leaves genetically, so exhibits very lovely figure from spring to fall. The growth rate is slightly slower than that of a normal 'Dawn Redwood'. The new variety becomes better in full sunlight or partial shade. The leaf color is extremely distinctive, that is bright yellow especially under strong sunlight. The new variety can be reproduced on a commercial scale by cutting or grafting.

2 Drawing Sheets

BACKGROUND OF NEW VARIETY

The present invention comprises a new and distinct variety of *Metasequoia glyptostroboides* ('Dawn Redwood').

The 'Dawn Redwood' is an excellent tree for landscaping in parks, golf fields, streets or river side. The leaves are deciduous, opposite in arrangement, and linear, flattened, straight or slightly curved, pectinately arranged, 1.25 cm long and 0.16 cm broad on mature trees. Its leaf color is bright green above changing to brown in fall and can be an excellent orange-brown to red brown. The habit is pyramidal, conical with a single straight trunk in youth, but, supposedly develop a broad-rounded crown with age. Furthermore, growth rate is fast (15 m in 15 to 20 years).

Conventionally, there are two varieties as follows.

(1) 'National'—Habit conspicously narrow — pyramidal, which was selected in 1958 at the National Arboretum. It showed 18 m high, 8.4 m wide at 23 years old.

(2) 'Sheridan Spire'—More upright than typical for the species.

Namely, two varieties are characterized by habit, especially branching pattern. However, as the leaf color is the same as compared with the common 'Dawn Redwood', they do not give a strong impact to us from a visual point of view.

The new variety of 'Dawn Redwood' is characterized by the leaf color and slightly slower growth rate. The new variety also roots readily through cutting with and without hormones or other root stimulating materials. The leaves are distinctly bright yellow as if its color is golden, especially observed under strong sunlight. Furthermore, the growth rate is slightly slower than the normal type, since the photosynthetic ability is lower as compared to the common 'Dawn Redwood' having green leaves.

The new variety has been found to retain its distinctive characteristics through successive propagations.

The new variety is a mutant introduced by x-ray irradiation. In April, 1974, approximately 200 g of *Metasequoia glyptostroboides* dry seeds were irradiated for one hour by 1000 R of x-ray. These treated seeds were sown into sowing boxes and raised by the routine method. Among 35,800 of treated seeds, approximately 28,000 of seed germinated and grew normally. But, 7,800 of the seeds could not germinate, perhaps due to damage from the X-ray treatment. Among the 28,000 seedlings, approximately 20,000 seedlings were healthy. From the 20,000 healthy seedlings, I discovered only one distinct seedling having bright yellow leaves. After selecting, this new and distinct individual has been propagated by repetitive cuttings. However, the characteristic has never changed, and always retained its distinctive characteristics.

In 1977, a parent stock (mutant) was planted at Kameyama Breeding Station, Institute for Forest Tree Improvement, New Oji Paper Co., Ltd. in Mie, Japan. In 1992, six individuals of this variety were planted at an arboretum in Kameyama Breeding Station to compare the characteristics with the common 'Dawn Redwoods' (common type).

SUMMARY OF THE INVENTION

The present new variety of *Metasequoia glyptostroboides* ('Dawn Redwood') generated from common type by x-ray radiation is characterized and distinguished from the common 'Dawn Redwood' and conventional varieties thereof, by its beautiful golden leaves, especially bright yellow leaves from the spring to the fall. The properties are very stable and are maintained during repeated propagations by cutting method.

DESCRIPTION OF THE NEW VARIETY

Figure 1:
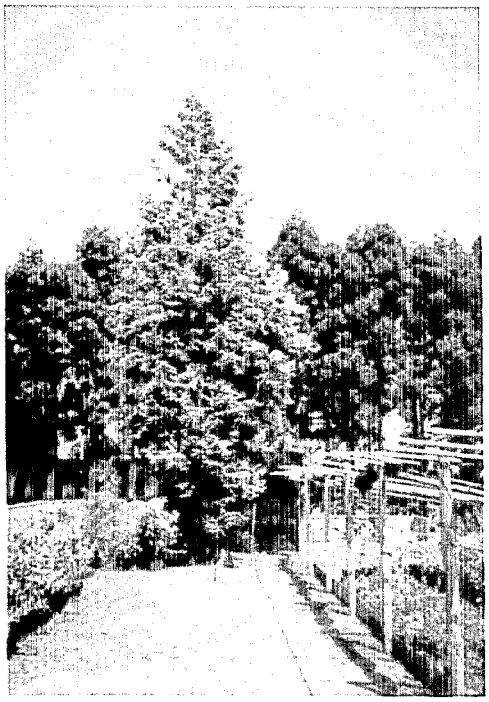
FIG. 1 is a photograph of the parent stock of the new variety, 'Golden Oji', being H=10.7 m, DBH=22.5 cm, in summer, at twenty years old in Kameyama.

The new variety is shown in FIG. 1 after a twenty year growth. The tree has a height of 10.7 meter and a width of 4.3 meter measured at the point of the greatest spread.

This habit is quite the same as the common type, showing the feathery-pyramidal growth habit. Its growth rate is considerably fast, but slightly slower than the common type. The bright yellow leaves makes this variety new and distinct as compared to the common type.

The mature leaves are deciduous, opposite in arrangement, lined flattened, straight or slightly curved, pectinately arranged, 1.25 cm long and 0.16 cm broad, upper surface is bright yellow like gold with a narrowly grooved midvein, lower surface bearing obscure lines of stomata, yellow green or slightly glaucous, the midrib slightly raised. Leaf color is bright yellow from spring to the fall, but changes from yellow to brown in the end of fall.

Figure 2:
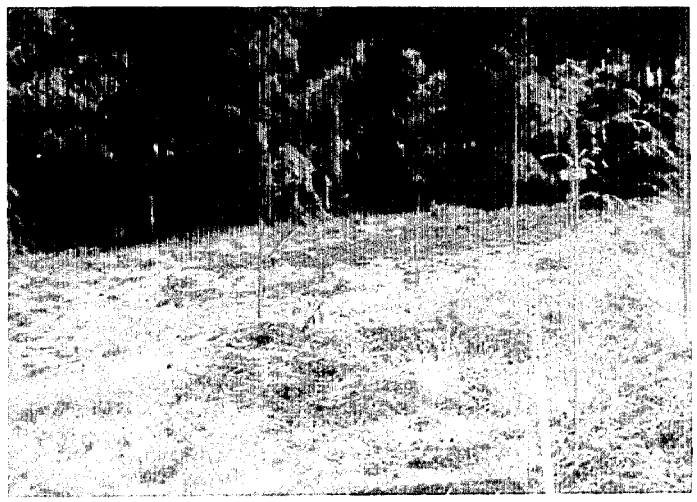
FIG. 2 is a photograph of the new variety, Golden Oji, of six years old, in fall, propagated by cutting from the parent stock at the arboretum in Kameyama.
Figure 3:
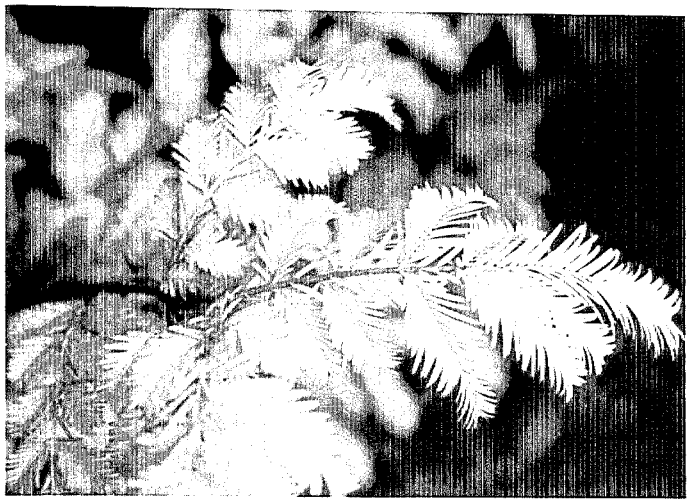
FIG. 3 is a photograph of its leaves showing bright yellow, like gold.
Figure 4:
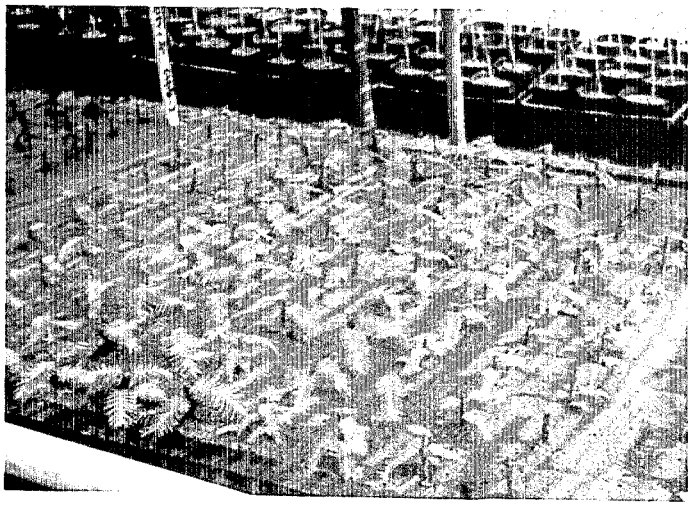
FIG. 4 is a photograph of propagation by cutting method, in outdoor cutting bed.

The growth rate, in height, of this new variety is slightly slower than the common type, as shown in FIG. 2. It seems to be owing to a decrease of photosynthetic ability induced by chloroplast mutation in leaves.

The bark of this variety is reddish brown when young, becoming darker, fissured and exfoliating in long narrow strips; base buttressing and developing and irregular fluted character.

In respect to disease and insects, there was no known serious problem. Japanese beetles rarely feed on the leaves. We can easily propagate this variety by the cutting method. First, the branches are cut from the parent stock in the end of February, and after arranging cuttings of 10 cm long, keep these arranged cuttings in a refrigerator at 5° C. until April. Second, place these in an outdoor rooting bed with or without hormone (IBA), obtaining a rooting rate of approximately 60%, 4 months after placing.

The oldest specimen of this tree did not come into flower until the current year, at 20 years of age. However, based on the assumption that the golden leaf color is controlled by homo-type recessive genes, it is likely that progeny from self-pollinating seed from this tree would also bear the genetic coding for leaf color if this tree proves to be fertile. Based on the same assumption, in crosses with 'Dawn Redwood' trees of normal foliage color, it would be expected that the unique and novel leaf color of this tree would be lost in the resulting hybrid progeny. However, the lack of precocious seeding of this tree does not prevent the multiplication of trees with the highly desirable foliage coloration through asexual production. Accordingly, the population of this tree will be increased through steps of asexual propagation, by rooting cuttings.

Foliage color of the new variety, 'Golden Oji', was compared with that of common type as follows.

One-year leaf receiving enough sunlight was obtained from the parent stock in May, and the color tone of the surfaces of leaf was measured by a CHROMA METER CR-200 (Minolta).

The color difference (ΔE) between the 'Golden Oji' (G.O.) and the common type (cont.) was calculated by the following equation:

$$\Delta E \times E(\text{cont.})-E(G.O.)\ (E=\sqrt{L^2+a^2+b^2},$$

wherein "L" represented "value", "a" represents hue, and "b" represents Chroma.

The degree of the color difference was evaluated as follows:

| ΔE | Evaluation |
|---|---|
| 0–0.5 | trace |
| 0.5–1.5 | slight |
| 1.5–3.0 | noticeable |
| 3.0–6.0 | appreciable |
| 6.0–12.0 | much |
| 12.0< | very much |

The following result was obtained.

| Variety | Symbol L | a | b | E | Evaluation |
|---|---|---|---|---|---|
| (1) Common type | −34.57 | −18.15 | 18.23 | 44.10 | |
| (2) Golden Oji | −16.32 | −11.34 | 39.30 | 38.75 | . Yellow is stronger, brighter according to the data of b and L. |
| Color difference | | | | ΔE = 5.35 | |

Another evaluation of the exposed leaf color of the 20-year-old 'Golden Oji' and the common type tree was performed using the Japanese Color Dictionary of Horticulture with the following results:
1) 'Golden Oji'; 7Y 2704, bright greenish yellow
2) Common Type; 5GY 3508, dark yellow green

DESCRIPTION OF THE VARIETY

The botanical characteristics of the new and distinct variety of *Metasequoia glyptostroboides* ('Dawn Redwood') with variety name 'Golden Oji' are as follows:

Genus: Metasequoia.

Commercial name: Dawn Redwood.

General characteristics:

*Leaves.*—Deciduous, opposite in arrangement, linear, flattened, straight or slightly curved, pectinately arranged 1.25 cm long and 0.16 cm broad.

*Leaf color.*—Bright green above changed to brown in fall; can be excellent orange-brown to red-brown.

*Habit.*—Pyramidal, conical, with a single straight trunk in youth.

*Growth rate.*—Fast (15 m in 15 to 20 years).

Breeding program: Radiation breeding strategy by x-ray.

*Material.*—Dry seeds of 200 g.

*X-ray radiation.*—1000 R for one hour. The rate of mutation by the radiation treatment performed is estimated to have been about one in 20,000.

Trade name: 'Golden Oji' (variety name).

Parentage. *Metasequoia glyptostroboides* (common type).

Similarities to parentage:

*Leaf arrangement.*—Midrib, and stomata.

*Bud arrangement and its shape, stem characteristics.*—Habit, (feathery-pyramidal growth), Bark (reddish brown).

*Diseases and insect.*—Hardly any.

*Propagation.*—Cutting or grafting easy.

Differences to parentage:

*Leaf color.*—Bright yellow like gold, especially under strong sunlight.

*Growth rate.*—slightly slower for example, in 5-year-old, the common type; 151 cm high, 2.1 cm wide at the base, but a new variety; 120 cm high, 1.8 cm wide at the base.

*Flower.*—No appearance until 20-years-old.

Location and character where plant were discovered: Kameyama Breeding Station, Mie, Japan. This variety was not discovered naturally, but induced artificially by x-ray irradiation. This mutant had a distinct characteristic having bright yellow leaves.

Location where first asexually reproduced: Nursery at Kameyama Breeding Station.

Climatic conditions under which tree was grown:

*Mean annual temperature.*—15.7° C. (Max Temp. 27.3° C. in August, Min Temp. 5° C. in February).

*Mean annual rainfall.*—1706 mm (Max 292 mm in June, Min 29 mm in December).

Tree:

*Habit.*—Feathery-pyramidal with a single straight trunk.

*Growth rate.*—Slightly slower in the height (approximately 80% of the common type).

*Height.*—10.7 m in 20-year-old (22.5 cm DBH).

*Spread.*—4.7 m in 20-year-old.

*Hardiness.*—Strong.

*Disease resistance.*—Hardly any problems.

*Seed production.*—No, as the flowers have not appeared.

*Effects of weather.*—Growth is affected by temperature and rainfall.

*Soil conditions.*—Sandy loam is best, but can grow at clay-rich soil.

*Wind resistance.*—Strong.

*Propagation.*—Easy by cutting (60% of rooting rate) or grafting.

As this variety is a mutant of chloroplast controlled by recessive gene, its propagation method is limited by asexual propagation.

*Bud break period.*—Spring, from April.

Branches:

*Branch pattern.*—Feathery-conical, dense.

*Length.*—Middle (Length/Height×100=14%).

*Color.*—Reddish-brown.

Foliage:

*Size.*—1.25 cm long, 0.16 cm broad on mature trees.

*Arrangement.*—Opposite, pectinately.

*Shape.*—Linear, flattened, straight or slightly curved.

*Top side.*—Gradually becoming shorter in the length.

*Underside.*—Gradually becoming shorter in the length.

*Ribs and veins.*—Upper surface; narrowly grooved. Lower surface; slightly raised.

*Ribs and vein color.*—Upper surface; white yellow. Lower surface; yellow-brown.

*Margin.*—Smooth.

*Leaf tips.*—Acuminate.

*Leaf base.*—Slightly round.

*Color.*—Bright yellow like gold.

*Fall color.*—Reddish brown.

*Leaf bud break period.*—Spring, mainly from April.

Bark:

*Color.*—Reddish brown when young, becoming darker.

*Texture.*—Fine in leaf, less so when defoliated.

*Appearance.*—Fissured and exfoliating in long narrow strips; base buttressing and developing an irregular fluted character.

Fruit:

*Size.*—We have been not able to find any fruit until 20-year-old.

Flower:

*Male.*—The inventor has been not able to find any flower until 20-years old.

*Female.*—The inventor has been not able to find any flower until 20-years old.

USAGE AND MAINTENANCE

The new variety, called 'Golden Oji', of 'Dawn Redwood' is valuable for landscape ornaments. The new variety has beautiful golden leaves, and exhibits very lovely figure from spring to fall, especially in full sunlight or partial shade. The leaf color is extremely distinctive, bright yellow especially under strong sunlight. The new variety can be reproduced on a commercial scale by cutting or grafting.

The new variety of the present invention named 'Golden Oji' is now maintained in Kameyama Breeding Station, Institute for Forest Type Improvement, New Oji Paper Co. Ltd. in Mie preference, Japan.

I claim:

1. A new and distinctive variety of *Metasequoia glyptostroboides* ('Dawn Redwood'), substantially as herein illustrated and described, characterized particularly as to novelty by that the color of leave is bright yellow like gold especially in summer changing to brown in fall, and that the growth rate is slightly slower than the normal type.

* * * * *